United States Patent [19]
Beitler

[11] Patent Number: 5,782,238
[45] Date of Patent: Jul. 21, 1998

[54] MULTIPLE ELECTRODE EKG DEVICE

[76] Inventor: Martin M. Beitler, 115 Spring St., New York, N.Y. 10012

[21] Appl. No.: 563,264

[22] Filed: Nov. 27, 1995

[51] Int. Cl.$^6$ .................................................. A61B 5/0408
[52] U.S. Cl. .................................... 128/639; 128/644
[58] Field of Search .............................. 128/639, 644; 607/148, 149

[56] References Cited

U.S. PATENT DOCUMENTS

| | | |
|---|---|---|
| 4,027,664 | 6/1977 | Heavner, Jr. et al. . |
| 4,121,575 | 10/1978 | Mills et al. ............................ 128/644 |
| 4,202,344 | 5/1980 | Mills et al. ............................ 128/644 |
| 4,498,480 | 2/1985 | Mortensen . |
| 4,763,660 | 8/1988 | Kroll et al. . |
| 4,858,617 | 8/1989 | Sanders . |
| 5,184,620 | 2/1993 | Cudahy et al. . |
| 5,224,479 | 7/1993 | Sekine . |
| 5,257,631 | 11/1993 | Wilk . |
| 5,353,793 | 10/1994 | Bornn . |

FOREIGN PATENT DOCUMENTS 274612  7/1951  Switzerland ............................ 128/644

OTHER PUBLICATIONS

Barr et al, "A Device for Rapid ECG Monitoing", Anaesthesia, vol. 27, No. 1, Jan. 1972, pp. 94–96.

*Primary Examiner*—Lee S. Cohen
*Attorney, Agent, or Firm*—Kilpatrick Stockton LLP; John S. Pratt; Richard A. Clegg

[57] ABSTRACT

A flexible multiple electrode EKG device is disclosed for hooking a patient to an electrocardiograph instrument, which is capable of being used with a variety of different sized patients. The assembly comprise a pad having sufficient weight to ensure that the pad will conform closely to the outer surface of the patient's chest when in place. A plurality of sets of electrodes are embedded in the pad, with each set of electrodes corresponding to a particular body size. A switch is provided for selectively activating the appropriate set of electrodes, depending on the size of the patient, to ensure optimal positioning of the electrodes.

10 Claims, 2 Drawing Sheets

MULTIPLE ELECTRODE EKG DEVICE

BACKGROUND OF THE INVENTION

1. Field of the Invention

This invention relates generally to electrocardiographs. More particularly, the invention relates to an EKG device comprising a pad with multiple EKG electrodes, that is positioned onto a patient's chest for the purpose of conducting electrocardiograph tests. Individual electrodes, or sets of electrodes, can be selectively activated or deactivated, depending on the size of a particular patient.

2. Discussion of the Prior Art

An electrocardiograph is an instrument used to record the various electrical impulses that are generated by the heart to produce contractions or heartbeats. The impulses are measured by electrodes and are recorded on paper or displayed on a monitor for examination. The display of the electrical impulses provides a variety of information to a treating physician regarding the patient's heart. The tracing, or hardcopy, provides a valuable baseline recording and can indicate abnormalities that may require further treatment.

Typically, an electrocardiograph (or EKG) tracing is produced by attaching ten individual electrodes to the surface of the patient's body, one electrode to each limb and six at specific points on the patient's chest, with each of the chest electrodes corresponding approximately to a particular area of the patient's heart. An electrical lead extends from each of the electrodes to an electrocardiograph instrument, which receives the input signals and produces either a signal on a monitor screen or a hard copy of the data, often with some degree of interpretation. In a typical "EKG" analysis, six precordial leads and 4 limb leads are used; the position of each must be approximated to a predetermined location on the patient's chest or limbs.

Often, electrocardiograph tests are conducted in emergency situations such as when a patient is experiencing chest pain. In such emergency situations, the patient is often sweaty, short of breath and uncomfortable. Accordingly, the various electrodes used to obtain the necessary information about the status of the heart's function must be attached to the patient's body quickly, and must be positioned properly. In a typical EKG procedure, each electrode must be individually positioned on the patient's body. Proper positioning of the electrodes requires the attention of a skilled nurse, technician, or doctor. In an emergency situation, the time spent attaching each individual electrode to the patient can delay further treatment, and can thus have serious consequences. Further, the electrodes, which are typically held onto the patient's skin by adhesive, often detach due to movement of the patient, or due to perspiration, body hair or skin cream on the patient's body.

To date, a variety of probe pads or belts have been developed, which are designed to facilitate placement of electrocardiograph electrodes onto a patient's body. However, none of the devices has adequately addressed the problem in a practical manner. Some cannot be adequately adjusted to work with patients of varying body sizes and shapes. Others can be adjusted to a limited extent, but only after they have been placed around the patient's upper torso and fastened in place. Others, such as the assembly described in U.S. Pat. No. 4,498,480, provide a pad assembly that does not require wrapping around the patient's torso. However, the assembly includes only a single set of electrodes, with the position of each electrode being capable of minimal adjustment. Thus, it will not adequately conform to patients with a wide range of different chest sizes. In addition, the pad is not uniformly weighted across its entire surface. Instead, weights are fastened to the lateral ends of the pad, which will tend to pull the pad tautly across the patient's chest. This can cause the pad to bridge across the patient's breasts, causing the electrodes positioned between the breasts to lose contact with the surface of the chest. In addition, the apparatus requires the electrical leads to be attached separately and laboriously to the EKG instrument. As a result, the leads can become tangled, or can be easily disturbed by the movements of the patient, doctor, or nurse, causing the electrodes to be pulled away from the patient's chest.

Accordingly, it is a basic object of the present invention to provide an improved multiple electrode device that overcomes the above-described deficiencies of the prior art. It is the general object of the invention to provide an electrode device that can be easily positioned onto patients having a variety of chest sizes and shapes, with switching means that allows a physician to rapidly activate a desired pattern of electrodes for a given patient by selectively activating or deactivating specific electrodes or sets of electrodes.

It is a further object of the present invention to provide an improved electrode device that will conform closely to the surface of a patient's chest, providing consistent and complete contact between the individual electrodes and the patient's chest.

It is a further object of the present invention to provide an electrode device that allows standardized lead placement procedures, regardless of patient size.

It is a further object of the present invention to provide an improved electrode device that is easy and economical to design and construct, and is adaptable to a variety of different technologies, including those presently existing for EKG's.

It is a further object of the present invention to provide an improved electrode device that is easily cleaned, and thus reusable, providing cost savings to hospitals and patients.

SUMMARY OF THE INVENTION

As will be apparent from the discussion below, these and number of additional objects are accomplished by the present invention.

In a basic aspect, the invention is a flexible multiple electrode EKG device for use in positioning electrodes onto a patient to facilitate the use of an electrocardiograph instrument. The assembly comprises a flexible pad with multiple electrodes embedded therein, extending through the lower surface of the pad. The electrodes are grouped into plural sets of electrodes, each set containing those electrodes that are positioned to correspond to a particular body size or shape. For a given patient, the desired set of electrodes can be selectively activated or deactivated by a switching means, to ensure the use of optimally positioned electrodes regardless of the size of the patient. The pad is uniformly weighted across its surface, to provide consistent contact between the electrodes and the patients' chest, without bridging across the patient's breasts.

The present apparatus provides a number of advantages over the prior art. The pad can be quickly positioned on a patient without the need to position individual probes, and without fastening the pad via straps attached to the patient's back. The pad can also be used with different patients having a variety of chest sizes and shapes. The uniform, flexible weighting of the pad prevents bridging across the patient's breasts, to ensure constant and adequate contact of each individual electrode to the patient's chest throughout the

3

"EKG" analysis. The invention also avoids disengagement from the chest due to sweating, movement, hair, body cream or oils. As a result of these features, the invention standardizes lead placement from institution to institution, providing consistent results from test to test, and dramatically improving the comparability of previous electrocardiographs to current tracings.

The apparatus is also economical and simple in design, yet durable and highly effective in use. The apparatus can also be easily cleaned, making it totally reusable. As a result, the apparatus decreases hospital and patient costs by eliminating the need to purchase disposable adhesive electrodes. The apparatus also dramatically reduces the time spent positioning electrodes on the patient, thus reducing the time the EKG machine is engaged.

The apparatus is also easy to design, construct and use, with color coding of the various electrode positions to ensure accurate placement on the patient, regardless of the patient's size or body type. The apparatus is also completely adaptable to existing EKG technologies and can be readily used with existing EKG devices. As a result, it can be easily used by hospital personnel trained with typical EKG equipment, as well as by other personnel with less experience.

DESCRIPTION OF THE PREFERRED EMBODIMENTS

Figure 1:
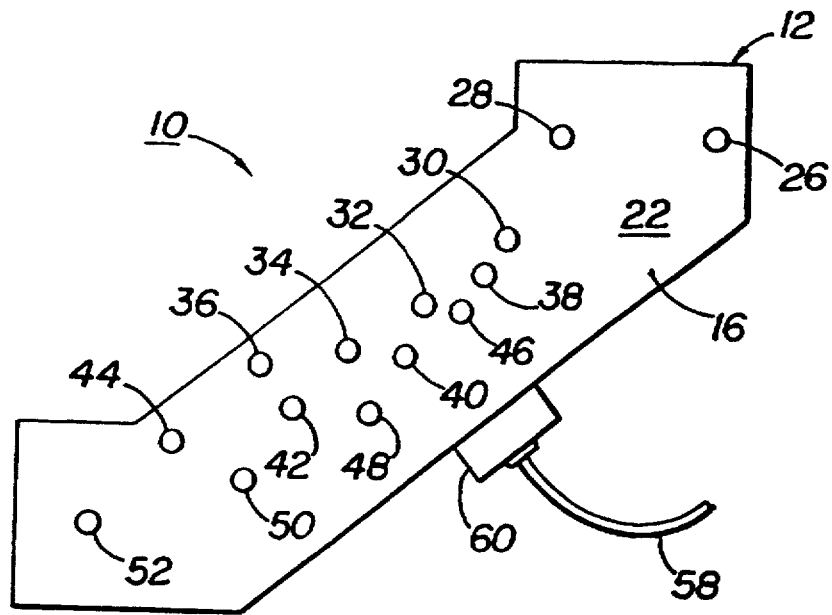
FIG. 1 of the drawing is a bottom plan view of a preferred embodiment of the present invention, showing the overall structure of the apparatus and the relative positions of the various electrodes.
Figure 2:
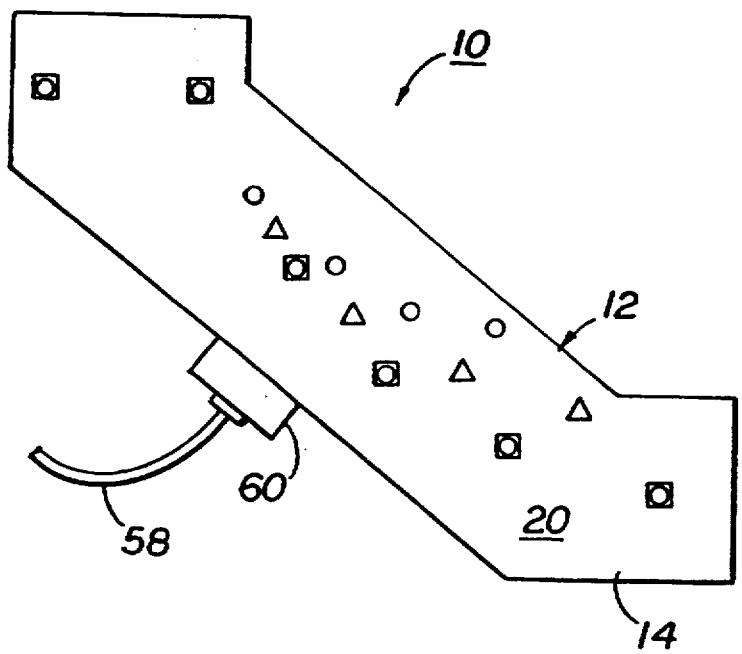
FIG. 2 of the drawing is a top plan view of the embodiment shown in FIG. 1.

Turning to FIGS. 1 and 2, a preferred embodiment of an electrode assembly 10 of the present invention comprises a flat pad 12, with multiple sets of electrodes embedded therein. The pad 12 is approximately 40 cm by 28 cm in size, which allows the pad to cover the central chest region of a patient, while extending to cover the left portion of the chest.

Figure 3:
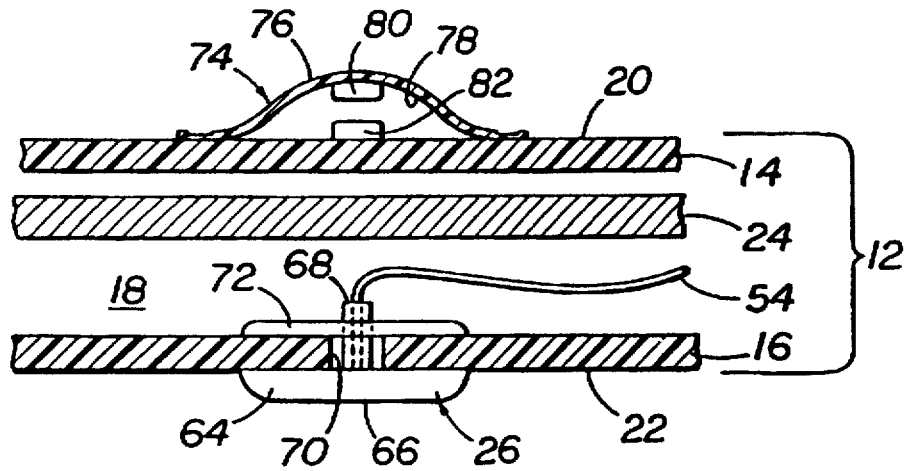
FIG. 3 of the drawing is a cross-section view of a portion of the embodiment shown in FIG. 1, showing the details of an individual electrode.

The pad has an upper sheet 14, as shown in FIG. 2, and a lower sheet 16, as shown in FIG. 1, which are sandwiched together and joined along their respective perimeters, forming an interior region 18 between the two sheets 14 and 16, as shown in FIG. 3. The upper sheet 14 defines the upper surface 20 of the pad 12, which faces upward when the pad is positioned onto a patient. The lower sheet 16 defines the lower surface 22 of the pad 12, which faces against the patient's chest when the pad is positioned onto the patient. The upper sheet 14 and the lower sheet 16 of the pad 12 are preferably made of vinyl, or other like material, with a non-skid surface. Preferably, the upper and lower sheets can be disconnected from one another along at least one side of the pad, to allow manual access into the interior region 18 for maintenance purposes.

The pad 12 is uniformly weighted across its entire surface, to ensure that the pad 12 will conform to the contours of the patient's chest, and retain contact with the chest surface at

4 all times, without bridging across the patient's breasts. In the two-sheet embodiment described above, this is accomplished by positioning a flexible sheet of weighted material 24 between the upper sheet 14 and the lower sheet 16, as shown in FIG. 3. Preferably, the weighted sheet 24 is a sheet of lead, approximately 3/16 thick, with approximately the same shape as the upper and lower sheets 14 and 16. Alternatively, a plurality of discrete weights can be fastened at regular intervals throughout the pad 12, to provide a substantially uniform weight distribution across the overall surface of the pad.

As shown in FIG. 1, the device includes a plurality of electrodes, which are exposed through the lower surface 22 of the pad 12. The electrodes constitute a plurality of separate sets of electrodes, with each set of electrodes including those electrodes that are appropriately positioned for use with a patient having a particular body size or shape. The first set of electrodes includes electrodes 26, 28, 30, 32, 34 and 36. These electrodes are set in positions that would be appropriate for a standard EKG of a relatively small person. The second set of electrodes includes electrodes 26 and 28 (in common with the first set of electrodes) and electrodes 38, 40, 42 and 44. These electrodes are set in positions that would be appropriate for a standard EKG of a medium sized person. The third set of electrodes includes electrodes 26 and 28 (in common with the first and second sets of electrodes) and electrodes 46, 48, 50 and 52. These electrodes are set in positions that would be appropriate for a standard EKG of a relatively large sized person.

The approximate positions of the various electrodes in the most preferred embodiment can be expressed in terms of a two-dimensional x-y Cartesian coordinate system, with the origin (0,0) of the coordinate system corresponding to the position of electrode 26. Based on the specific orientation of the pad shown in FIG. 1, the preferred approximate positions of the remaining electrodes, in terms of centimeters, are set forth in Table 1.

TABLE 1

| Electrode | Coordinate Position (cm) |
| --- | --- |
| 28 | −8,0 |
| 30 | −11,−5 |
| 32 | −14,−8 |
| 34 | −19,−11 |
| 36 | −23,−12 |
| 38 | −12,−7 |
| 40 | −17,−12 |
| 42 | −22,−14 |
| 44 | −28,−16 |
| 46 | −13,−9 |
| 48 | −18,−14 |
| 50 | −24,−18 |
| 52 | −32,−20 |

Figure 4:
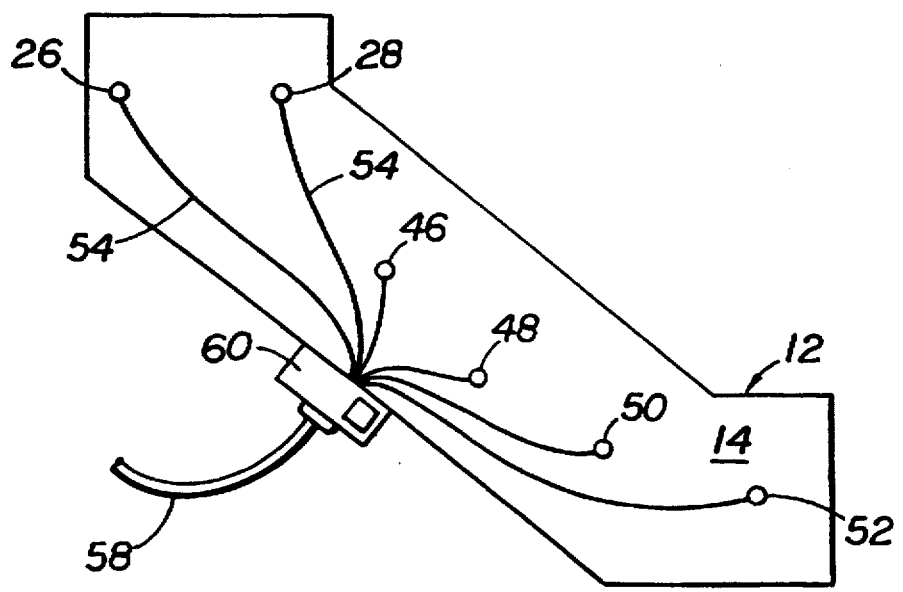
FIG. 4 of the drawing shows the embodiment of FIG. 2, with the upper sheet and the weighted sheet removed to expose the leads for a single set of electrodes.

Turning to FIGS. 3 and 4, a lead 54 extends from each electrode, within the interior region 18 of the pad 12. Each lead 54 extends to a switch assembly 60, for selectively activating or deactivating either the first, second or third set of electrodes. This allows the most optimally positioned set of electrodes to be selected for a given patient, ensuring the best location for signal monitoring. Alternatively, the switch assembly 60 can allow each individual electrode to be independently activated or deactivated. It should be understood that the term switch as used herein includes switch assemblies that incorporate multiple individual switches. The term switch is also not limited to mechanical switches, and includes any device, including an electrical circuit or microprocessor, that is capable of selectively activating or deactivating any of the electrodes.

The switch 60 is preferably positioned along the outer perimeter of the pad 12, such that the individual leads 54 are completely contained within the pad 12. The signals from each of the selected electrodes are transmitted from the switch assembly 60 to an EKG instrument through wires (not shown) housed within a conduit or sheath 58. The wires terminate at a single plug assembly, which is received by a receptacle on the EKG instrument.

While the electrodes 26-52 are visible on the lower surface 22 of the pad 12, they are not directly visible on the upper surface 20 of the pad 12. Thus, to aid the technician or physician in positioning the pad 12 onto a patient's chest, the position of each electrode is indicated on the upper surface 20, as shown in FIG. 2, for instance, by the use of a colored indicator, or a number, or both. Preferably, each set of electrodes has a unique color identifying that particular set of electrodes. For instance, each electrode in the first set of electrodes may have a blue identifier, each electrode in the second set of electrodes may have a green identifier, and each electrode in the third set of electrodes may have a red identifier. For convenience in understanding the Figures, the first, second and third sets of electrodes are identified by triangles, circles, and squares, respectively, in FIG. 2. The position of electrodes 26 and 28, which are common to all three sets of electrodes, are identified in FIG. 2 as circles within squares. Where number codes or color codes are used to identify individual electrodes, the corresponding numbers or colors can also appear on the switching means 60, to associate a given switch position with a given electrode or a given set of electrodes.

In FIG. 3, the details of an individual electrode are shown by reference to electrode 26 of FIG. 1. The electrode 26 has a nickel/silver contact 64, with a lower contact surface 66 that is exposed to the chest of the patient on the lower surface 22 of the pad 12. A hollow post 68 extends upward from the contact 64, into the interior 18 of the pad 12, through a hole 70 in the lower vinyl sheet 16. A clip 72 grips the outer surface of the hollow post 68, squeezing the lower vinyl sheet 16 between the clip 72 and the contact 64, and holding the electrode 26 firmly in position. To ensure that the electrode will be firmly held by the clip 72, the surface of the post 68 can be threaded or roughened. Alternatively, a slight indentation can be provided on each side of the post 68, for engaging the inner surface of a U-shaped clip 72. The lead 54 extends from the contact 64 into the interior region 18 of the pad, through the hollow post 68. As shown in FIG. 4, the lead 54 from each electrode then extends through the hollow interior 18 of the pad 12 to the switch 60.

As discussed above, the various electrodes can be grouped into discrete sets of electrodes, with an entire set of electrodes being activated or deactivated at once via the switch assembly 60. Alternatively, each electrode can be individually activated or deactivated, to allow greater flexibility in choosing a desired electrode pattern for a given patient. This can be accomplished through the use of a switch assembly 60 that contains an individual on-off switch or setting for each electrode, rather than for each set of electrodes. It can also be accomplished by associating with each electrode an individual pressure-activated switch that is positioned on the surface 20 of the upper sheet 14, at a position corresponding to that of the electrode.

For instance, as shown in FIG. 3, a flexible, hollow bubble-shaped button 74, having an outer surface 76 and an inner surface 78, can be provided on the surface 20, at a position corresponding to the position of a particular electrode. A first electrical contact 80 is attached to the inner surface of the 78 of the button. A second electrical contact 82 is positioned underneath the first electrical contact 80. An electrical lead (not shown) extends from each contact. When the outer surface 76 of the button 74 is depressed downward by a fingertip, the first electrical contact 80 contacts the second electrical contact 82, completing a switching circuit to activate or deactivate the desired electrode. With this embodiment, a physician merely places the pad onto the patient, and presses the buttons that correspond to the specific electrodes that are desired for the test. In a particularly preferred embodiment, the EKG machine registers which of the individual electrodes have been activated for a particular test, to facilitate inter-institutional and inter-current comparison of different EKG tests.

In general use, the apparatus 10 is placed onto a patient's chest, with the lower surface 22 of the pad 12 in full contact with the surface of the chest. The proper electrodes for use with the given patient are determined by visual inspection, and by reference to the numerical or color identifiers on the upper surface 20 of the pad 12, and the appropriate switch settings are set on the switch 60 (or through the use of the buttons 74 described above) to activate the desired electrodes. The limb leads, which are not incorporated into the pad 12, are attached to the patient in a normal manner, and the electrocardiograph is carried out in a normal manner. After the test has been conducted, the apparatus 10 is easily removed, and can be wiped clean for reuse with another patient.

As discussed above, the present invention is easy to design, construct and use. The invention is also completely adaptable to and can be readily used with existing EKG technology. As a result, the present invention can be easily used by hospital personnel trained with typical EKG equipment or by other personnel with less experience.

While in the foregoing, there have been described various preferred embodiments of the present invention, it should be understood to those skilled in the art that various modifications and changes can be made without departing from the true spirit and scope of the invention as recited in the foregoing claims.

What is claimed is:

1. An apparatus for positioning electrodes onto a patient to facilitate the use of an electrocardiograph instrument, said apparatus comprising:
    a) a flexible pad having an upper surface and a lower surface, said pad having sufficient uniform weight across its entirety such that the lower surface of the pad will maintain substantially complete contact with a patient's chest when the pad is positioned thereon;
    b) a plurality of sets of electrodes exposed through the lower surface of the pad;
    c) an electrical lead associated with each individual electrode for connecting said electrode to an electrocardiograph machine; and
    d) a switch for preferentially activating or deactivating each electrode, whereby a specific desired pattern of activated electrodes can be achieved, depending on the size of the patient.

2. The apparatus of claim 1, wherein each set of electrodes has a desired pattern of electrodes corresponding to a particular patient body size.

3. The apparatus of claim 2, wherein the switch for selectively for activating or deactivating each electrode also activates or deactivates the other electrodes in the same set as that electrode.

4. The apparatus of claim 2, wherein there are three sets of electrodes.

5. The apparatus of claim 4, wherein each of the three sets of electrodes comprises six electrodes.

6. The apparatus of claim 5, wherein two of the electrodes within each set of electrodes are common electrodes shared by each of the three sets of electrodes.

7. An apparatus for positioning electrodes onto a patient to facilitate the use of an electrocardiograph instrument, said apparatus comprising:
   a) a flexible pad having an upper surface and a lower surface, said pad having sufficient uniform weight across its entirety such that the lower surface of the pad will maintain substantially complete contact with a patient's chest when the pad is positioned thereon;
   b) a plurality of electrodes exposed through the lower surface of the pad;
   c) an electrical lead associated with each individual electrode for connecting said electrode to an electrocardiograph machine; and
   d) a switch for preferentially activating or deactivating each electrode, whereby a specific desired pattern of activated electrodes can be achieved, depending on the size of the patient, wherein the flexible pad comprises
   (i) an upper sheet of material and a lower sheet of material, said upper and lower sheets of material positioned adjacent to one another and connected to one another along their respective perimeters, forming an interior region therebetween; and
   (ii) a uniformly weighted sheet positioned within the interior region, said weighted sheet having sufficient weight whereby the lower surface of the flexible pad will maintain substantially complete contact with a patient's chest when placed upon the chest.

8. The apparatus of claim 7, wherein the weighted sheet is lead.

9. The apparatus of claim 7, wherein the specific position of each individual electrode is indicated on the upper sheet of the pad.

10. An apparatus for positioning electrodes onto a patient to facilitate the use of an electrocardiograph instrument, said apparatus comprising:
   a) a flexible pad having an upper surface and a lower surface, said pad having sufficient uniform weight across its entirety such that the lower surface of the pad will maintain substantially complete contact with a patient's chest when the pad is positioned thereon;
   b) a plurality of electrodes exposed through the lower surface of the pad;
   c) an electrical lead associated with each individual electrode for connecting said electrode to an electrocardiograph machine; and
   d) a switch for preferentially activating or deactivating each electrode, whereby a specific desired pattern of activated electrodes can be achieved, depending on the size of the patient, wherein a separate pressure-activated switch is associated with each of the electrodes, said pressure activated switch positioned on the upper surface of the pad at a position corresponding to the position of the associated electrode.

* * * * *